United States Patent
Sugihara et al.

(10) Patent No.: US 8,076,462 B2
(45) Date of Patent: Dec. 13, 2011

(54) METHOD FOR PRODUCING ANTITHROMBIN COMPOSITION

(75) Inventors: Tsutomu Sugihara, Gunma (JP); Setsuko Onodera, Tokyo (JP); Tomonari Urakubo, Gunma (JP); Toshiyuki Suzawa, Gunma (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 0 days.

(21) Appl. No.: 12/594,423

(22) PCT Filed: Apr. 2, 2008

(86) PCT No.: PCT/JP2008/056600
§ 371 (c)(1),
(2), (4) Date: Oct. 2, 2009

(87) PCT Pub. No.: WO2008/120801
PCT Pub. Date: Oct. 9, 2008

(65) Prior Publication Data
US 2010/0113754 A1    May 6, 2010

(30) Foreign Application Priority Data
Apr. 2, 2007    (JP) ................................ 2007-096179

(51) Int. Cl.
*C07K 14/47*    (2006.01)

(52) U.S. Cl. ........................................ 530/393; 530/350

(58) Field of Classification Search ................... 530/393, 530/350
See application file for complete search history.

(56) References Cited

U.S. PATENT DOCUMENTS

2010/0113754 A1 * 5/2010 Sugihara et al. .............. 530/393

FOREIGN PATENT DOCUMENTS

| EP | 0339919 A2 | 11/1989 |
| JP | 2852307 B2 | 8/1990 |
| JP | 2003-520805 A | 7/2003 |
| JP | 2003-520806 A | 7/2003 |
| WO | 01/53328 A1 | 7/2001 |
| WO | 01/53329 A1 | 7/2001 |

OTHER PUBLICATIONS

Extended European Search Report dated Apr. 19, 2010 in European Application No. 08739710.5.
A. Morrica, et al., "Manufacturing process of Anti-thrombin III concentrate: viral safety validation studies and effect of column re-use on viral clearance," Biologicals, vol. 31, No. 3, pp. 165-173 (2003).
International Search Report (PCT/ISA/210) issued on May 13, 2008 in the corresponding PCT Application No. PCT/JP2008/056600 in the name of Kyowa Hakko Kirin Co., Ltd.
Written Opinion of the International Searching Authority (PCT/ISA/237) issued on May 13, 2008 in the corresponding PCT Application No. PCT/JP2008/056600 in the name of Kyowa Hakko Kirin Co., Ltd.
"Chisso Chromatography Jutenzai Cellufine. Affinity Chromatography-yo Gel. Cellufine Sulfate" Chisso Corp., 2006. pp. 1-3. Retrieved from http://www.chisso.co.jp/fine/jp/cellufine/grade/grade-1.html#02.
Peterson, C. B. et., al. "Isolation and Characterization of an Antithrombin III Variant with Reduced Carbohydrate Content and Enhanced Heparin Binding" The Journal of Biological Chemistry, Jan. 10, 1985, vol. 260, No. 1, pp. 610-615.
Lindsay, M et., al. "Purification of recombinant DNA-derived factor IX produced in transgenic pig milk and fractionation of active and inactive subpopulations" Journal of Chromatography A, 2004, vol. 1026, pp. 149-157.
Mochizuki, S. et., al. "Purification and characterization of recombinant human antithrombin containing the prelatent form in Chinese hamster ovary cells" Protein Expression and Purification, 2005, vol. 41, pp. 323-331.
Edmunds, T. et., al. "Transgenically Produced Human Antithrombin: Structural and Functional Comparison to Human Plasma—Derived Antithrombin", Blood, Jun. 15, 1998, vol. 91, No. 12, pp. 4561-4571.
Japanese Patent Office, Application No. JP 2009-507556, Notification of Reasons for Refusal dated Apr. 26, 2011 (in the name of Kyowa Hakko Kirin Co., Ltd.).
European Search Report issued on Jun. 20, 2011 in the corresponding European Patent Application No. 08739710.5.

* cited by examiner

*Primary Examiner* — Chih-Min Kam
(74) *Attorney, Agent, or Firm* — Sughrue Mion, PLLC

(57) ABSTRACT

The provision of an antithrombin composition having a desired α-form content rate or β-form content rate is required. The invention provides a process for producing an antithrombin composition having a desired α-form content rate or β-form content rate which is prepared by contacting an antithrombin-containing aqueous solution with a Cellufine Sulfate chromatography carrier.

14 Claims, No Drawings

METHOD FOR PRODUCING ANTITHROMBIN COMPOSITION

CROSS-REFERENCE TO RELATED APPLICATIONS

This application is a 371 National Stage Entry of International Application No. PCT/JP2008/056600, filed Apr. 2, 2008, which claims benefit of Japanese Patent Application No. 2007-096179, filed Apr. 2, 2007. The entire disclosures of the prior applications are considered part of the disclosure of the present application and are incorporated herein by reference.

TECHNICAL FIELD

This invention relates to a process for producing an antithrombin composition. Particularly, it relates to a process for producing an antithrombin composition having a desired α-form content rate or β-form content rate from an antithrombin-containing aqueous solution.

BACKGROUND OF THE INVENTION

Antithrombin is an important blood coagulation inhibition system factor (a serine protease inhibitor) in blood, which inhibits activity of a serine protease that relates to blood coagulation and the like by irreversibly forming a stable complex with a serine protease in a one molecule-to-one molecule manner. Antithrombin is mainly synthesized in liver and is present in human blood plasma in an amount of about 150 mg/l (Non-patent Reference 1).

Antithrombin is a glycoprotein comprising 432 amino acids and having a molecular weight of approximately 59,000 to 65,000, and has three disulfide bonds, Cys8-Cys128, Cys21-Cys95 and Cys247-Cys430, in its molecule. N-Glycoside-linked sugar chains are added to 4 positions, the 96th, 135th, 155th and 192nd asparagine residues counting from the N-terminus (hereinafter referred to as Asn96, Asn135, Asn155 and Asn192, respectively) of antithrombin. The antithrombin in human plasma exists in two kinds of isoforms, α-form (α type) having four N-glycoside-linked sugar chains and β-form (β type) having only three N-glycoside-linked sugar chains but not having a sugar chain to the Asn135 (Non-patent Reference 2, Non-patent Reference 3). The sugar chain N-glycoside-linked to antithrombin is a complex sugar chain comprising N-acetylglucosamine, sialic acid, galactose and mannose and has sialic acid on its terminal. The larger the binding number of sialic acids bound to the sugar chain terminal is, the longer the half-life of a glycoprotein in blood is. It is said that this is because when the sialic acid is eliminated, the galactose residue exposed to the non-reducing-end group is captured by an asialoglycoprotein (a galactose receptor localized in the liver) and quickly degraded (Non-patent Reference 4, Non-patent Reference 5). In addition, the antithrombin easily is changed into an inactive form (latent form) by a physical stress, such as heat, or a chemical stress, such as an acid (Non-patent Reference 6).

From 90 to 95% of the antithrombin in human blood plasma is composed of the α-form, and the remaining 5 to 10% is composed of the β-form (Non-patent Reference 2). In addition, about 70% of the sugar chains bound to the antithrombin in human blood plasma have two sialic acids per sugar chain, and the remaining, about 30% of the sugar chains, have one sialic acid per sugar chain (Non-patent Reference 1, Non-patent Reference 7).

The antithrombin purified from human blood plasma is used as a therapeutic agent for thrombosis based on congenital antithrombin deficiency and disseminated intravascular coagulation (DIC) which accompanies lowering of antithrombin. However, the antithrombin purified from human blood plasma has a danger of causing contamination with blood-derived viruses such as AIDS virus and human parvovirus, mutation type Creutzfeldt-Jakob disease factor, transmissible spongiform encephalopathy (TSE) factor and the like. Based on such a background, in recent years, a recombinant antithrombin has been attempted to produce from an animal cell, such as Chinese hamster ovary cell (CHO cell), or a transgenic animal, using recombinant techniques.

Unlike the human blood plasma-derived antithrombin purification product, the antithrombin obtained from an antithrombin-producing recombinant CHO cell or transgenic animal is a mixture of α-form, β-form, latent form, inactive precursor (prelatent form) or associated form of the antithrombin, host-derived impurities and the like. In addition, the number of sialic acids bound to the sugar chain terminal is also irregular (Non-patent Reference 8, Non-patent Reference 9).

As the purification method of antithrombin, heparin chromatography (Non-patent Reference 3), cation exchange chromatography (Patent Reference 1), hydroxyapatite chromatography (Patent Reference 2), hydrophilic chromatography (Non-patent Reference 8, Non-patent Reference 9, Patent Reference 3, Patent Reference 4) and the like are known. However, nothing is known about the process for preparing an antithrombin composition having a desired α-form or β-form content rate from a mixture of α-form, β-form, latent form, prelatent form and associated form.

Non-Patent Reference 1: The Second Series of Pharmaceutical Research, 20, 185 (1992)
Non-Patent Reference 2: Japanese Journal of Thrombosis and Hemostasis, 10, 93 (1999)
Non-Patent Reference 3: J. Biol. Chem., 260, 610 (1985)
Non-Patent Reference 4: Sequences of protein of immunological interest Fourth Edition, Public Health Service National Institutes of Health (1987)
Non-Patent Reference 5: Blood, 73, 84 (1987)
Non-Patent Reference 6: Structure, 2, 257 (1994)
Non-Patent Reference 7: Arch. Biochem. Biophys., 203, 458 (1980)
Non-Patent Reference 8: Protein Expression and Purification, 41, 323 (2005)
Non-Patent Reference 9: Blood, 91, 4561 (1998)
Patent Reference 1: JP-A-2003-520805
Patent Reference 2: JP-A-2003-520806
Patent Reference 3: JP Patent 2852307
Patent Reference 4: JP Patent 2678249

DISCLOSURE OF THE INVENTION

Problems that the Invention is to Solve

An object of the invention is to provide a process for producing an antithrombin composition having a desired α-form or β-form content rate from an antithrombin-containing aqueous solution, with a high yield.

Means for Solving the Problems

The invention relates the following (1) to (11):
(1) A process for producing an antithrombin composition, comprising contacting an antithrombin-containing aqueous solution with a Cellufine® Sulfate chromatography (cellulose sulfate ester chromatography) carrier to thereby prepare an antithrombin composition having a desired α-form or β-form content rate;

(2) A process for producing an antithrombin composition, comprising contacting an antithrombin-containing aqueous solution with a Cellufine® Sulfate chromatography (cellulose sulfate ester chromatography) carrier and eluting antithrombin compositions adsorbed onto the carrier by increasing a conductivity of an eluent to thereby prepare an antithrombin composition having a desired α-form or β-form content rate from the eluate;

(3) A process for producing an antithrombin composition, comprising contacting a conductivity-adjusted antithrombin-containing aqueous solution with a Cellufine® Sulfate chromatography (cellulose sulfate ester chromatography) carrier to thereby prepare an antithrombin composition having a desired α-form or β-form content rate from a fraction unadsorbed onto the carrier;

(4) The process according to any one of (1) to (3), which further comprises carrying out anion exchange chromatography and/or hydrophobic chromatography;

(5) The process according to (4), wherein the hydrophobic chromatography is carried out after carrying out said preparation described in any one of (1) to (3);

(6) The process according to any one of (1) to (5), wherein the antithrombin composition comprises an antithrombin in which sugar chains bound to the antithrombin contained in the composition have 1 or more to 3 or less sialic acids in average per sugar chain;

(7) The process according to any one of (1) to (5), wherein the antithrombin composition comprises an antithrombin in which sugar chains bound to the antithrombin contained in the composition have 1.5 or more to 2.5 or less sialic acids in average per sugar chain;

(8) The process according to (6) or (7), wherein the sugar chains bound to the antithrombin are 3 or 4 sugar chains;

(9) The process according to any one of (1) to (6), wherein the antithrombin composition comprises an antithrombin in which sugar chains bound to the antithrombin contained in the composition have 3 or more to 12 or less sialic acids in average per antithrombin;

(10) The process according to any one of (1) to (6), wherein the antithrombin composition comprises an antithrombin in which sugar chains bound to the antithrombin contained in the composition have 6 or more to 8 or less sialic acids in average per antithrombin; and

(11) An antithrombin composition produced by the process according to any one of (1) to (10).

Advantageous Effects of the Invention

The invention provides a method for producing an antithrombin composition having a desired α-form or β-form content rate from an antithrombin-containing aqueous solution, with a high yield. An antithrombin composition prepared by the process of the invention is useful as a medicament.

BEST MODE FOR CARRYING OUT THE INVENTION

The invention relates to a process for producing an antithrombin composition having a desired α-form or β-form content rate, which comprises contacting an antithrombin-containing aqueous solution with a Cellufine Sulfate chromatography carrier.

In the invention, the antithrombin-containing aqueous solution may be any aqueous solution as long as it contains an antithrombin. Example of the antithrombin-containing aqueous solution includes aqueous solutions which contain α-form, β-form, latent form, prelatent form, associated form, N-terminal or C-terminal deletion form, amino acid modification form, sugar chain substitution form, antithrombin derivatives, host cell-derived impurities, production process-derived impurities or the like. In addition, various additive agents, such as a sialidase inhibitor (e.g., sialic acid), may be included in the antithrombin-containing aqueous solution. Example of the sialidase inhibitor include certain species of sialic acid, namely N-acetylneuraminic acid derivative, such as N-acetylneuraminic acid, 2,3-dehydro-2-deoxy-N-acetylneuraminic acid (also called as 5-acetamido-2,6-anhydro-3,5-dideoxy-D-glycero-D-galacto-non-2-enoic acid, or Neu5Ac2en or 2,3-D) [Handbook of Enzyme Inhibitor $3^{rd}$, revived and enlarged edition Part A, Wiley-VCH, Weinheim (1999), U.S. Pat. No. 5,510,261, Glycobiology, 3, 201, (1993)]; copper chloride [Biotech. Bioeng., 55, 390 (1997), Biotechnology, 13, 692 (1995), U.S. Pat. No. 6,528,286]; an antibody to sialidase (JP-T-8-510133 (the term "JP-T" as used herein means a published Japanese translation of a PCT patent application), WO 2007/108464); and the like.

In the invention, examples of the antithrombin include human antithrombin; amino acid modification form, addition form, deletion form, substitution form or sugar chain modification form of human antithrombin; antithrombin derivatives; and the like. Further specifically, examples of the antithrombin include an antithrombin obtained from the living body, such as blood plasma or urine; an antithrombin obtained by culturing an antithrombin-producing cell established using a recombinant technique or a cell fusion technique; an antithrombin obtained from a transgenic non-human animal or plant; and the like.

Examples of the cell which produces antithrombin include a transfected cell into which human antithrombin gene has been introduced. Specific examples of the transfected cell include a cell prepared by introducing an antithrombin gene into a cell, such as an animal cell, a plant cell or a yeast cell; more specifically a Chinese hamster ovary cell (CHO cell), a NS0 cell which is a mouse myeloma cell, a SP2/0 cell, a rat myeloma YB2/0 cell, an IR983F cell, a BHK cell which is a syrian hamster kidney origin, a Namalwa cell which is a human myeloma cell, an embryonic stem cell, a fertilized egg cell and the like.

The medium for culturing a cell which can produce the antithrombin is not limited as long as it is a medium which is appropriate for culturing respective cells. As a medium for culturing an animal cell, a general basal medium which is used for culturing animal cells can be used. Examples of the medium for culturing an animal cell include a serum-containing medium, a medium which does not contain animal-derived components, such as serum albumin or a serum fraction; a serum-free medium; a protein-free medium; and the like. Among these, a serum-free medium or a protein-free medium is preferably used. For example, RPMI 1640 medium [The Journal of the American Medical Association, 199, 519 (1967)], Eagle's MEM medium [Science, 122, 501 (1952)], Dulbecco's modified MEM (DMEM) medium [Virology, 8, 396 (1959)], 199 medium [Proceedings of the Society for the Biological Medicine, 73, 1 (1950)], F12 medium [Proc. Natl. Acad. Sci. USA, 53, 288 (1965)], Iscove's modified Dulbecco's medium (IMDM medium) [J. Experimental Medicine, 147, 923 (1978)], EX-CELL™ 302 medium, EX-CELL™-CD-CHO and EX-CELL™ 325 medium (all manufactured by SAFC Bioscience), CD-CHO™ medium and CD DG 44™ medium (all manufactured by Invitrogen), IS CD-CHO™ medium (manufactured by Irvine Scientific); or a modified medium, mixed medium or concentrated medium thereof, and the like can be used. Among these, RPMI 1640 medium, DMEM medium, F12 medium, IMDM medium, EX-CELL™ 302 medium, CD-CHO™ medium, IS CD-CHO™ medium or the like is preferably used.

Also, a physiologically active substance, a nutrient factor or the like which is necessary for the growth of a cell that can produce the antithrombin composition can be added thereto, if necessary. These additives are included in the medium in advance before the culturing, and/or additionally-supplied to the medium liquid as a supplementary medium or supplementary solution during the culturing. Method for additionally-supplying may be in any form such as one solution or a mixed solution of two or more kinds. And the method for additionally-supplying may be either continuous or intermittent.

In addition, when a transfected animal cell into which human antithrombin gene has been introduced is cultured, the osmotic pressure suitable for culturing the cell or producing the antithrombin composition is 200 to 600 mOsm/kg, preferably 250 to 500 mOsm/kg, more preferably 250 to 400 mOsm/kg.

Examples of the transgenic non-human animal or plant which can produce the antithrombin include a non-human animal or plant into which the human antithrombin gene has been introduced. Specific examples of the animal to be used include mouse, rat, guinea pig, hamster, rabbit, dog, sheep, pig, goat, cattle, monkey and the like. Specific Examples of the plant include tobacco, potato, tomato, carrot, soybean, rape, alfalfa, rice, wheat, barley, corn and the like.

Furthermore, in the invention, examples of the antithrombin-containing aqueous solution also include, in addition to those which are obtained from the living body, such as blood plasma or urine containing antithrombin, an aqueous antithrombin solution obtained in the purification step. Specifically, examples of the antithrombin obtained in the purification step include a cell-removed solution, an alcohol fraction solution, a salting-out fraction solution, a heparin affinity chromatography eluate, an ion exchange chromatography eluate, an ion exchange membrane eluate, a gel filtration chromatography eluate, a hydrophobic chromatography eluate and the like.

Examples of the cell-removed solution include solutions obtained by removing the cells from an antithrombin-containing aqueous solution obtained from the living body, such as blood plasma or urine; an antithrombin-containing aqueous solution obtained from a transgenic non-human animal or plant; an antithrombin-containing aqueous solution obtained from a cell established using a recombinant technique; an antithrombin-containing aqueous solution obtained in the purification step; and the like. Specific examples include a solution obtained by removing the cells from a cell culture solution by a centrifugation method, a cross flow filtration method (tangential flow filtration method), a filtration method by a depth filter, a filtration method by a membrane filter, a dialysis method, or a combined method thereof.

Examples of the alcohol fraction solution include fraction solutions prepared by adding alcohol and the like to an antithrombin-containing aqueous solution obtained from the living body, such as blood plasma or urine; an antithrombin-containing aqueous solution obtained from a transgenic non-human animal or plant; an antithrombin-containing aqueous solution obtained from a cell established using a recombinant DNA technique; an antithrombin-containing aqueous solution obtained in the purification step, and the like. Specific examples of the alcohol fraction solution include a fraction solution obtained by a low temperature ethanol fractionation method or the like.

Examples of the salting-out fraction solution include fraction solutions prepared by adding a salt, such as ammonium sulfate, sodium sulfate, sodium citrate, sodium chloride or potassium chloride to an antithrombin-containing aqueous solution obtained from the living body, such as blood plasma or urine; an antithrombin-containing aqueous solution obtained from a transgenic non-human animal or plant; an antithrombin-containing aqueous solution obtained from a cell established using a recombinant technique; an antithrombin-containing aqueous solution obtained in the purification step; and the like, to thereby precipitate antithrombin.

Examples of the heparin affinity chromatography eluate include antithrombin eluate obtained by contacting an antithrombin-containing aqueous solution obtained from the living body, such as blood plasma or urine; an antithrombin-containing aqueous solution obtained from a transgenic non-human animal or plant; an antithrombin-containing aqueous solution obtained from a cell established using a recombinant technique; an antithrombin-containing aqueous solution obtained in the purification step; and the like, with a carrier in which a molecule having affinity for antithrombin, such as heparin, is bound to a base carrier, such as a polymer composed of cellulose, agarose, silica, chitosan or the like to thereby adsorb antithrombin, eluting the antithrombin with an appropriate eluent, to thereby unadsorb them, and the like. Examples of the heparin affinity chromatography carrier include Heparin Sepharose 6 Fast Flow (manufactured by GE Healthcare), Procep-Heparin (manufactured by Millipore), TOYOPEARL AF-Heparin-650 (manufactured by Tosoh), Heparin HyperD (manufactured by Pall) and the like.

Examples of the ion exchange chromatography eluate or ion exchange membrane eluate include antithrombin eluate obtained by contacting an antithrombin-containing aqueous solution obtained from the living body, such as blood plasma or urine; an antithrombin-containing aqueous solution obtained from a transgenic non-human animal or plant; an antithrombin-containing aqueous solution obtained from a cell established using a recombinant technique; an antithrombin-containing aqueous solution obtained in the purification step; and the like, with a carrier in which a molecule having an ion exchange group, such as sulfate group, methylsulfate group, sulfophenyl group, carboxymethyl group, quaternary ammonium group, quaternary aminoethyl group, diethylaminoethyl group or the like, is bound to a base carrier or a membrane, such as a polymer constituted from cellulose, agarose, silica, chitosan or the like to thereby adsorb antithrombin, eluting the antithrombin with an appropriate eluent, to thereby unadsorb them, and the like. Examples of an ion exchange chromatography carrier or an ion exchange membrane carrier include Q Sepharose Fast Flow, SP Sepharose Fast Flow, DEAE Sepharose Fast Flow, CM Sepharose Fast Flow, Capto Q, Capto S (manufactured by GE Healthcare), TOYOPEARL DEAE-650, TOYOPEARL SuperQ-650, TOYOPEARL QAE-550, TOYOPEARL SP-650, TOYOPEARL CM-650, TOYOPEARL SP-550, TOYOPEARL MegaCap SP-550 (all manufactured by Tosoh), Macro-Prep High S, UNOsphare S, Macro-Prep CM, MacroPrep High Q, UNOsphare Q, Macro-Prep DEAE (all manufactured by Bio-Rad Laboratories), DEAE Spherodex, SP Spherodex, DEAE Trisacryl, CM Trisacryl, SP Trisacryl, Q HyperZ, CM HyperZ, Q Ceramic HyperD, S Ceramic HyperD, DEAE Ceramic HyperD, CM Ceramic HyperD, Mustang Q, Mustang S (all manufactured by Pall), Sartobind S, Sartobind Q, Sartobind C, Sartobind D (all manufactured by Sartorius), Fractogel TMAE(M), Fractogel TMAE(S), Fractogel TMAE HiCap(M), Fractogel DEAE(M), Fractogel DEAE(S), Fractogel DMAE(M), Fractogel DMAE (S), Lactogel SO3-(M), Fractogel SO3-(S), Fractogel SEHiCap(M), Fractogel COO-(M), Fractogel COO-(S) (all manufactured by Merck), DEAE Cellufine A-500, QA Cellufine Q-500 (all manufactured by Chisso), CHITO PEARL "Basic", DEAE CHITO PEARL, Carboxylated CHITO PEARL, Sulfonated CHITO PEARL (all manufactured by Fujibo Holdings) and the like.

Examples of the gel filtration chromatography eluate include antithrombin solutions fractionated based on molecular weights, prepared by contacting an antithrombin-containing aqueous solution obtained from the living body, such as blood plasma or urine; an antithrombin-containing aqueous solution obtained from a transgenic non-human animal or plant; an antithrombin-containing aqueous solution obtained from a cell established using a recombinant technique; an antithrombin-containing aqueous solution obtained in the purification step, and the like, with a carrier in which is bound to a base carrier, such as a polymer constituted from cellulose, agarose, silica, chitosan or the like to thereby adsorb antithrombin, eluting the antithrombins with an appropriate eluent and the like. Examples of a gel filtration chromatography carrier include Superdex 75, Superdex 200, Superdex 75 prep grade, Superdex 200 prep grade, Superose 6, Superose 12, Superose 6 prep grade, Superose 12 prep grade, Sephacryl S-100 HR, Sephacryl S-200 HR, Sephacryl S-300 HR, Sephacryl S-400 HR, Sephacryl S-500 HR (all manufactured by GE Healthcare), TOYOPEARL HW-40, TOYOPEARL HW-50, TOYOPEARL HW-55, TOYOPEARL HW-65, TOYOPEARL HW-75 (all manufactured by Tosoh), Biogel P (manufactured by Bio-Rad Laboratories), Trisacryl, Ultrogel (all manufactured by Pall), Fractogel BioSEC (manufactured by Merck), Cellulofine GH-25 (manufactured by Chisso) and the like.

Examples of the hydrophobic chromatography eluate include antithrombin eluate obtained by contacting an antithrombin-containing aqueous solution obtained from the living body, such as blood plasma or urine; an antithrombin-containing aqueous solution obtained from a transgenic non-human animal or plant; an antithrombin-containing aqueous solution obtained from a cell established using a recombinant technique; an antithrombin-containing aqueous solution obtained in the purification step; and the like, with a carrier in which a molecule having hydrophobic property, such as methyl group, ethyl group, propyl group, isopropyl group, butyl group, tert-butyl group, octyl group, ether group or phenyl group, is bound to a base carrier, such as a polymer composed of cellulose, agarose, silica or chitosan to thereby adsorb and elute with an appropriate eluent, or to thereby unadsorb, and the like. Examples of a hydrophobic chromatography carrier include Phenyl Sepharose 6 Fast Flow (high-sub), Phenyl Sepharose 6 Fast Flow (low-sub), Octyl Sepharose 4 Fast Flow, Butyl Sepharose 4 Fast Flow (all manufactured by GE Healthcare), TOYOPEARL Hexyl-650, TOYOPEARL Butyl-650, TOYOPEARL Phenyl-650, TOYOPEARL Ether-650, TOYOPEARL PPG-600, TOYOPEARL Butyl-600, TOYOPEARL Super Butyl-550 (all manufactured by Tosoh), Mactro-Prep t-Butyl, Macro-Prep Methyl (all manufactured by Bio-Rad Laboratories), QMA Spherosil, Methyl Ceramic HyperD (all manufactured by Pall), Fractogel Phenyl (S), Fractogel Propyl(S) (all manufactured by Merck), Phenyl-Cellulofine (all manufactured by Chisso), Butylated CHITO PEARL, Phenylated CHITO PEARL (all manufactured by Fujibo Holdings) and the like.

Examples of the Cellufine Sulfate chromatography carrier in the invention include Cellufine Sulfate m, Cellufine Sulfate c, Sulfated Cellulofine m, Sulfated Cellulofine c, Sulfated Cellufine m, Sulfated Cellufine c (all manufactured by Chisso) and the like.

In the invention, the antithrombin composition having a desired α-form or β-form content rate can be prepared by contacting an antithrombin-containing aqueous solution with a Cellufine Sulfate chromatography carrier. The preparation process may be a recovery of antithrombin from the fraction of the antithrombin composition in which antithrombin are adsorbed onto the carrier or a recovery of antithrombin from the fraction of the antithrombin composition in which antithrombin is unadsorbed onto the carrier. For example, an antithrombin composition having a desired α-form or β-form content rate can be prepared by contacting an antithrombin-containing aqueous solution with a Cellufine Sulfate chromatography carrier to thereby adsorb the antithrombin composition, and then combining appropriate fractions of the fractionated solution obtained by eluting the antithrombin composition with a conductivity-adjusted buffer solution.

In the invention, an adsorbing condition of the antithrombin composition to a Cellufine Sulfate chromatography carrier is a pH 5 to 9, preferably pH 5 to 8. The loaded amount of antithrombin par 1 mL carrier is preferably 0.01 to 10 mg/mL, more preferably 0.1 to 5 mg/mL. The conductivity is preferably 0.01 mS/cm to 50 mS/cm, more preferably 0.1 to 20 mS/cm. Examples of the salts which constitute the buffer solution include a phosphate, a citrate, an acetate, a succinate, a maleate, a borate, Tris (base), HEPES, MES, PIPES, MOPS, TES, Tricine and the like. The concentration of these salts is preferably 0.01 mol/L to 0.5 mol/L, more preferably 0.02 mol/L. In addition, when the above-mentioned salt may be used in combination with other salts, such as sodium chloride, potassium chloride, sodium sulfate, or ammonium sulfate, at a concentration of 0.01 mol/L to 0.5 mol/L, the concentration of the salts which constitute the buffer solution is 0.001 mol/L to 1 mol/L. Specific Examples of a composition of the buffer solution include 20 mmol/L sodium phosphate (pH 6.0), 20 mmol/L sodium citrate (pH 6.0) and the like.

The antithrombin composition adsorbed onto the Cellufine Sulfate chromatography carrier is eluted by increasing the conductivity of the buffer solution. In order to obtain a desired composition, it may be eluted with a buffer solution having an appropriate pH and conductivity. The buffer solution for eluting has pH 5 to 9, more preferably pH 5 to 8. The conductivity is preferably 0.01 to 300 mS/cm, more preferably 0.1 to 250 mS/cm. The elution method may be either a method in which antithrombin is eluted by increasing the salt concentration in a stepwise manner or a method in which antithrombin is eluted by increasing the salt concentration continuously (a gradient method). Examples of the buffer solution for eluting include a phosphate, a citrate, an acetate, a succinate, a maleate, a borate, Tris (base), HEPES, MES, PIPES, MOPS, TES, Tricine and the like. The concentration of these salts is preferably 0.01 mol/L to 0.5 mol/L, more preferably 0.02 mol/L. The concentration of these is preferably 0.01 mol/L to 0.5 mol/L, more preferably 0.02 mol/L. In addition, the above-mentioned salts may be used in combination with other salts, such as sodium chloride, potassium chloride, sodium sulfate or ammonium sulfate, at a concentration of 0.001 mol/L to 4 mol/L. Specific examples of the buffer solution for eluting include 20 mmol/L sodium phosphate buffer (pH 6.0) including 1 mol/L sodium chloride, 20 mmol/L sodium citrate buffer (pH 6.0) including 1 mol/L sodium chloride, and the like.

In addition, for example, the antithrombin composition having a desired α-form or β-form content rate can also be prepared by contacting an antithrombin-containing aqueous solution with a Cellufine Sulfate chromatography carrier, and then collecting the fractions unadsorbed onto the carrier, followed by combining appropriate fractions of the thus obtained fractionated solution.

Specifically, the antithrombin composition can be recovered from the unadsorbed fractions without adsorbing the antithrombin composition onto the Cellufine Sulfate chromatography carrier, by adjusting the conductivity of the antithrombin-containing aqueous solution and the adsorbed amount of antithrombin per unit volume of the carrier in advance, to thereby contact the antithrombin-containing aqueous solution with the carrier. The conductivity of the antithrombin-containing aqueous solution to be contacted is preferably 0.01 mS/cm to 100 mS/cm, more preferably 0.1 mS/cm to 50 mS/cm. The loaded amount of antithrombin per 1 mL carrier is preferably 0.01 to 50 mg/mL, more preferably 0.1 to 20 mg/ml. In addition, the pH is preferably 5 to 9, more preferably 5 to 8. Examples of the salts which constitute the buffer solution include a phosphate, a citrate, an acetate, a succinate, a maleate, a borate, Tris (base), HEPES, MES, PIPES, MOPS, TES, Tricine and the like. The concentration of these salts is preferably 0.01 mol/L to 0.5 mol/L, more preferably 0.02 mol/L. In addition, the above-mentioned salts may be used in combination with other salts, such as sodium chloride, potassium chloride, sodium sulfate, ammonium sulfate at a concentration of 0.01 mol/L to 0.5 mol/L, more preferably 0.01 mol/L to 0.5 mol/L. Specific examples of the buffer solution for eluting include 20 mmol/L sodium phosphate buffer (pH 6.0) including 0.01 mol/L to 0.5 mol/L of sodium chloride, 20 mmol/L sodium citrate buffer (pH 6.0) including 0.01 mol/L to 0.5 mol/L of sodium chloride, and the like.

In the invention, the α-form content rate means a ratio of α-form occupying to the total of α-form and β-form in the antithrombin composition. Though the antithrombin composition having a desired α-form content rate is obtained by the invention, the α-form content rate is preferably 80% or more, more preferably 90% or more, further preferably 95% or more, and particularly preferably 97% or more.

In the invention, the β-form content rate means a ratio of β-form occupying to the total of α-form and β-form in the antithrombin composition. Though the antithrombin composition having a desired β-form content rate is obtained by the invention, the β-form content rate is preferably 80% or more, more preferably 90% or more, further preferably 95% or more, and particularly preferably 97% or more.

In the invention, an antithrombin composition having a desired α-form content rate or β-form content rate can be obtained with a high yield by measuring the α-form content rate or β-form content rate in the fractionated solution collected from a Cellufine Sulfate chromatography and then combining appropriate fractions. Specifically, an antithrombin composition having an α-form content rate of 90% can be obtained at the rate of 50% or more, preferably 75% or more, as an α-form recovery rate. In addition, an antithrombin composition having a β-form content rate of 90% or more can be obtained at the rate of 50% or more, preferably 75% or more, as a β-form recovery rate.

In the invention, the α-form content rate or β-form content rate of antithrombin can be measured by heparin HPLC [J. Biol. Chem., 260, 610 (1985)], hydroxyapatite HPLC [Protein Expression and Purification, 28, 196 (2003), JP-T-2003-520806], miceller electrokinetic chromatography [J. Chromatography A, 924, 307, (2001), JP-A-2002-196004] and the like.

In addition, the invention relates to a process for producing an antithrombin composition by further combining the Cellufine Sulfate chromatography with anion exchange chromatography and/or hydrophobic chromatography.

In the invention, order of the combination of the Cellufine Sulfate chromatography with the anion exchange chromatography and/or the hydrophobic chromatography is not particularly limited. It is preferable to carry out the hydrophobic chromatography after carrying out the Cellufine Sulfate chromatography.

In the invention, in the case of the combination of the Cellufine Sulfate chromatography with the hydrophobic chromatography, the condition for contacting the antithrombin composition after carrying out the Cellufine Sulfate chromatography or the antithrombin-containing aqueous solution before carrying out the Cellufine Sulfate chromatography (hereinafter, both cases are generally called antithrombin-containing aqueous solution) with the hydrophobic chromatography is generally pH 5 to 9, preferably pH 5 to 8. The conductivity is generally 20 mS/cm or more, preferably 50 mS/cm or more. Example of the salts which constitute the buffer solution include a phosphate, a citrate, an acetate, a succinate, a maleate, a borate, Tris (base), HEPES, MES, PIPES, MOPS, TES, Tricine and the like. The concentration of these salts is preferably 0.01 mol/L to 0.5 mol/L, more preferably 0.02 mol/L. In addition, the above-mentioned salts may be used in combination with other salts, such as sodium chloride, potassium chloride, sodium sulfate or ammonium sulfate, at a concentration of 0 to 4 mol/L. Specific examples of the buffer solution for eluting include 20 mmol/L sodium phosphate buffer (pH 7.0) including 2 mol/L ammonium sulfate, 20 mmol/L sodium citrate buffer (pH 7.4) including 1 mol/L sodium sulfate, and the like.

The antithrombin composition adsorbed onto the hydrophobic chromatography carrier is eluted by decreasing conductivity of the buffer solution. The elution method may be either a method in which the antithrombin composition is eluted by decreasing the salt concentration in a stepwise manner (stepwise method) or a method in which the antithrombin composition is eluted by decreasing the salt concentration continuously (gradient method). Examples of the buffer solution for eluting include a phosphate, a citrate, a maleate, Tris (base), HEPES, MES, PIPES, MOPS, TES, Bicine, Tricine and the like. The concentration of these salts is preferably 0.01 mol/L to 0.5 mol/L, more preferably 0.02 mol/L. In addition, the above-mentioned salts may be used in combination with other salts, such as sodium chloride, potassium chloride, sodium sulfate, sodium citrate or ammonium sulfate at a concentration of 0 to 4 mol/L. Specific examples of the buffer solution for eluting include 20 mmol/L sodium phosphate buffer (pH 7.0), 20 mmol/L Tris buffer (pH 6.0), and the like.

In addition, by contacting an antithrombin-containing aqueous solution with a hydrophobic chromatography carrier, it is also possible to obtain a high purity antithrombin composition from a fraction unadsorbed onto the carrier. The contacting conditions to the hydrophobic chromatography carrier are generally pH 5 to 9, preferably pH 5 to 8. The conductivity of the antithrombin-containing aqueous solution to be contacted is preferably 1 to 300 mS/cm, more preferably 20 to 200 mS/cm. Examples of the buffer include a phosphate, a citrate, a maleate, Tris (base), HEPES, MES, PIPES, MOPS, TES, Bicine, Tricine and the like. The concentration of these salts is preferably 0.01 mol/L to 0.5 mol/L, more preferably 0.02 mol/L. In addition, the above-mentioned salts may be used in combination with other salts, such as sodium chloride, potassium chloride, sodium sulfate, sodium citrate or ammonium sulfate at a concentration of 0 to 2 mol/L. Specific examples of the buffer solution for contacting include 20 mmol/L sodium phosphate buffer (pH 7.0) including 1 mol/L ammonium sulfate, 20 mmol/L Tris buffer (pH 7.5) including 1 mol/L sodium sulfate, and the like.

A high purity antithrombin composition from which latent form, associated form, host cell-derived impurities, production process-derived impurities and the like are removed can be obtained by the above hydrophobic chromatography. In addition, even when the hydrophobic chromatography is carried out after carrying out the Cellufine Sulfate chromatography, the α-form content rate, β-form content rate or the binding number of sialic acids of the antithrombin composition obtained by the Cellufine Sulfate chromatography is maintained.

In the invention, in the case of the combination of the Cellufine Sulfate chromatography with the anion exchange chromatography, the condition for contacting an antithrombin-containing aqueous solution with the anion exchange chromatography carrier is generally pH 4 to 10, preferably pH 6 to 9. The conductivity of the antithrombin-containing aqueous solution to be contacted is preferably 0.01 mS/cm to 50 mS/cm, more preferably 0.1 mS/cm to 20 mS/cm. Examples of the salts which constitute the buffer solution include a phosphate, a citrate, an acetate, a succinate, a maleate, a borate, Tris (base), HEPES, MES, PIPES, MOPS, TES, Tricine and the like. The concentration of these salts is preferably 0.01 mol/L to 0.5 mol/L, more preferably 0.02 mol/L. In addition, the above-mentioned salts may be used in combination with other salts, such as sodium chloride, potassium chloride, sodium sulfate, sodium citrate or ammonium sulfate, at a concentration of 0.001 mol/L to 4 mol/L. Specific examples of the buffer solution for contacting include 20 mmol/L sodium phosphate buffer (pH 7.0) and 10 mmol/L Tris buffer (pH 7.4).

The antithrombin composition adsorbed onto the anion exchange chromatography carrier is eluted by increasing the conductivity of the buffer solution. The elution method may be any one of a method in which the substance of interest is eluted by applying to a column continuously for a certain period of time, a method in which the antithrombin composition is eluted by increasing the salt concentration in a stepwise manner (stepwise method) or a method in which the antithrombin composition is eluted by increasing the salt concentration continuously (gradient method). The buffer solution for eluting is preferably pH 4 to 10, more preferably pH 5 to 9. Examples of the salts which constitute the buffer solution include a phosphate, a citrate, an acetate, a succinate, a maleate, a borate, Tris (base), HEPES, MES, PIPES, MOPS, TES, Tricine and the like. The concentration of these salts is preferably 0.01 mol/L to 0.5 mol/L, more preferably 0.02 mol/L. In addition, the above-mentioned salts may be used in combination with other salts, such as sodium chloride, potassium chloride, sodium sulfate, sodium citrate or ammonium sulfate at a concentration of 0.001 mol/L to 4 mol/L. Specific examples of the buffer solution for eluting include 20 mmol/L sodium phosphate buffer (pH 7.0) including 1 mol/L sodium chloride, 20 mmol/L Tris buffer (pH 7.4) including 1 mol/L sodium chloride, and the like.

In addition, by contacting an antithrombin-containing aqueous solution with an anion exchange chromatography carrier, it is also possible to obtain a high purity antithrombin composition from a fraction unadsorbed onto the carrier. The condition for contacting the antithrombin-containing aqueous solution with the hydrophobic chromatography carrier is generally pH 4 to 10, preferably pH 5 to 9. The conductivity of the antithrombin-containing aqueous solution to be contacted is generally 0.01 to 100 mS/cm, preferably 0.1 to 50 mS/cm. Examples of buffer solution include a phosphate, a citrate, a maleate, Tris (base), HEPES, MES, PIPES, MOPS, TES, Bicine, Tricine and the like. The concentration of these is generally 0.01 mol/L to 0.5 mol/L, preferably 0.02 mol/L. In addition, the above-mentioned salts may be used in combination with other salts, such as sodium chloride, potassium chloride, sodium sulfate, sodium citrate or ammonium sulfate, at a concentration of 0.001 mol/L to 2 mol/L. Specific examples of the buffer solution for contacting include 20 mmol/L sodium phosphate buffer (pH 7.0) including 1 mol/L ammonium sulfate, 20 mmol/L Tris buffer (pH 7.5) including 1 mol/L sodium sulfate, and the like.

A high purity antithrombin composition from which a latent form, an associated form, host cell-derived impurities, production process-derived impurities and the like are removed can be obtained by the above anion exchange chromatography. In addition, even when the anion exchange chromatography is carried out after carrying out the Cellufine Sulfate chromatography, the α-form or β-form content rate of the antithrombin composition or the binding number of sialic acids is maintained.

In the invention, the latent form content rate of antithrombin can be measured by a hydrophobic HPLC method [Protein Expression and Purification, 21, 149 (2001)], a heparin HPLC method [Protein Expression and Purification, 33, 339 (2004)] or the like.

In the invention, the associated form content rate of antithrombin can be measured by a gel filtration HPLC method, a polyacrylamide gel electrophoresis method, a light scattering method, an ultracentrifugation method or the like.

The invention relates to a process for producing an antithrombin composition, wherein the antithrombin composition comprises an antithrombin in which sugar chains bound to the antithrombin contained in the composition have 1 or more to 3 or less sialic acids in average per sugar chain.

In addition, the invention relates to a process for producing an antithrombin composition, wherein the antithrombin composition comprises an antithrombin in which sugar chains bound to the antithrombin contained in the composition have 3 or more to 12 or less sialic acids in average per antithrombin.

In the invention, the binding number of sialic acids means average value of the sialic acids per antithrombin molecule which is composed of the composition. Since 3 or 4 of sugar chains bind to one antithrombin molecule, the binding number of sialic acids is 0 to 12 when sialic acid molecules of 0 to 3 per sugar chain bind to the sugar chain.

The number of sialic acids per sugar chain in the antithrombin composition obtained by the invention is preferably 1 or more to 3 or less in average, more preferably 1.5 or more to 2.5 or less in average. In addition, the antithrombin composition of the invention preferably has 3 or more to 12 or less sialic acids in average per antithrombin, more preferably has 6 or more to 8 or less sialic acids in average per antithrombin.

In the invention, the number of sialic acids per sugar chain is calculated by the following formula.

(The number of sialic acids per sugar chain)=(the binding number of sialic acids)/[4×(α-form content rate)+3×(β-form content rate)]

In the invention, the binding number of sialic acids of antithrombin can be measured by a fluorescent HPLC method [Anal. Biochem., 164, 138 (1987)], a resorcinol method or the like. In addition, the binding number of sialic acids can also be measured by an isoelectric focusing method, a capillary isoelectric focusing method or the like.

The invention is described further in more detail based on examples, but the invention is not limited to these examples.

EXAMPLES

Example 1

Preparation of Antithrombin-Containing Aqueous Solution (1)

An antithrombin-producing CHO cell line (FERM BP-8472) was cultured at 37° C. for 2 weeks in a medium prepared by adding 500 nmol/L of methotrexate (manufactured by Sigma Aldrich Fine Chemical) and 0.875 g/L of L-glutamine (manufactured by Wako Pure Chemical Industries) to EX-CELL™ 302 medium (manufactured by SAFC Bioscience) and then adjusting the osmotic pressure to 330 mOsm/kg, and the pH to 7.1. An antithrombin-containing aqueous solution 1 was obtained by passing the thus obtained culture broth (20 L) through a depth filter (manufactured by CUNO Inc., Zeta Plus Maximizer).

Preparation of Antithrombin-Containing Aqueous Solution (2)

An antithrombin-producing CHO cell line (FERM BP-8472) was cultured at 37° C. for 2 weeks in a medium prepared by adding 500 nmol/L of methotrexate (manufactured by Sigma Aldrich Fine Chemical) and 1.75 g/L of L-glutamine (manufactured by Wako Pure Chemical Industries) to EX-CELL™ 302 medium (manufactured by SAFC Bioscience, prepared to 1.3-fold concentration of the concentration described in the instructions attached thereto) and then adjusting the osmotic pressure to 330 mOsm/kg, and the pH to 7.1. An antithrombin-containing aqueous solution 2 was obtained by passing the thus obtained culture broth (20 L) trough a depth filter (manufactured by CUNO., Zeta Plus Maximizer).

Preparation of Antithrombin-Containing Aqueous Solution (3)

The antithrombin-containing aqueous solution 1 (6.2 L) was passed through a heparin column (Heparin Sepharose 6 Fast Flow, manufactured by GE Healthcare, column volume 524 ml, 4 mg load of an antithrombin composition per 1 ml carrier) which had been previously equilibrated with a buffer solution (50 mmol/L Tris, 14 mmol/L sodium citrate buffer, pH 7.4), to thereby adsorb the antithrombin composition to the column. After washing the column with a buffer solution (50 mmol/L Tris, 14 mmol/L sodium citrate buffer, pH 7.4, 10 column volumes), an antithrombin-containing aqueous solution 3 (3.68 liters) was obtained by eluting under a linear salt concentration gradient (10 column volumes) using a buffer solution (50 mmol/L Tris, 14 mmol/L sodium citrate buffer, pH 7.4) and another buffer solution (2.5 mol/L sodium chloride, 50 mmol/L Tris, 14 mmol/L sodium citrate buffer, pH 7.4).

Preparation of Antithrombin-Containing Aqueous Solution (4)

The antithrombin-containing aqueous solution 1 (36.1 L) concentrated to 1.65 L using an ultrafiltration membrane (Biomax 30, manufactured by Millipore), and then 6.6 L of purified water was added thereto. The obtained solution was passed through an anion exchange column (Q Sepharose Fast Flow, manufactured by GE Healthcare, column volume 76 mL) which had been previously equilibrated with a buffer solution (20 mmol/L sodium phosphate buffer, pH 7.0), to thereby adsorb the antithrombin composition onto the column. After washing the column with a buffer solution (20 mmol/L sodium phosphate buffer, pH 7.0, 0.5 column volumes), an antithrombin-containing aqueous solution 4 (505 mL) was obtained by eluting the antithrombin composition with a buffer solution (160 mmol/L sodium chloride, 20 mmol/L sodium phosphate buffer, pH 7.0, 0.5 column volumes).

Preparation of Antithrombin-Containing Aqueous Solution (5)

The antithrombin-containing aqueous solution 1 (1000 mL) was concentrated to 200 mL using an ultrafiltration membrane (Biomax 30, manufactured by Millipore). To 150 mL of the concentrated solution, 200 ml of purified water was added. Then 310 ml of the obtained solution was passed through an anion exchange chromatography column (Q Sepharose Fast Flow, manufactured by GE Healthcare, column volume 50 mL) which had been previously equilibrated with a buffer solution (50 mmol/L sodium chloride, 20 mmol/L sodium phosphate buffer, pH 7.0), to thereby adsorb antithrombin onto the column. After washing the column with a buffer solution (50 mmol/L sodium chloride, 20 mmol/L sodium phosphate buffer, pH 7.0), an antithrombin-containing composition 5 was obtained by eluting the antithrombin composition with a buffer solution (220 mmol/L sodium chloride, 20 mmol/L sodium phosphate buffer, pH 7.0).

Preparation of Antithrombin-Containing Aqueous Solution (6)

The antithrombin-containing aqueous solution 1 was concentrated 6-fold using an ultrafiltration membrane (Biomax 30, manufactured by Millipore). After adding a sialic acid solution (309.27 g/L, pH 7.0, and a buffer solution (20 mmol/L sodium phosphate buffer, pH 7.0, containing Triton X-100 and tributyl phosphate) thereto, purified water was further added thereto to adjust the conductivity to 4.8 mS/cm. The obtained solution was passed through an anion exchange chromatography column (Q Sepharose Fast Flow, manufactured by GE Healthcare) which had been previously equilibrated with a buffer solution (50 mmol/L sodium chloride, 20 mmol/L sodium phosphate buffer, pH 7.0), to thereby adsorb the antithrombin composition onto the column. After washing the column with a buffer solution (50 mmol/L sodium chloride, 20 mmol/L sodium phosphate buffer, pH 7.0), an antithrombin-containing aqueous solution 6 was obtained by eluting the antithrombin composition with a buffer solution (180 mmol/L sodium chloride, 20 mmol/L sodium phosphate buffer, pH 7.0).

Preparation of Antithrombin-Containing Aqueous Solution (7)

The antithrombin-containing aqueous solution 1 (650 mL) was concentrated to 33 mL using an ultrafiltration membrane (Biomax 10, manufactured by Millipore). To a 15.5 ml of the obtained solution, 23.2 mL of a buffer solution (150 mmol/L sodium chloride, 50 mmol/L Tris, 14 mmol/L sodium citrate buffer, pH 7.4) and 38.7 mL of another buffer solution (3 mol/L ammonium sulfate, 20 mmol/L sodium phosphate buffer, pH 7.4) was added. By carrying out centrifugation (15000 rpm, 15 minutes), the supernatant was collected. Then 74 mL of the obtained solution was passed through a hydrophobic column [Phenyl Sepharose 6 Fast Flow (high-sub), manufactured by GE Healthcare, column volume 4 ml] which had been previously equilibrated with a buffer solution (1.5 mol/L ammonium sulfate, 20 mmol/L sodium phosphate buffer, pH 7.4), to thereby adsorb the antithrombin composition onto the column. After washing the column with a buffer solution (1.5 mol/L ammonium sulfate, 20 mmol/L sodium phosphate buffer, pH 7.4), an antithrombin-containing aqueous solution 7 was obtained by eluting under a linear salt concentration gradient with a buffer solution (1.5 mol/L ammonium sulfate, 20 mmol/L sodium phosphate buffer, pH 7.4) and another buffer solution (20 mmol/L sodium phosphate buffer, pH 7.4).

Example 2

Preparation of Antithrombin Composition by Cellufine Sulfate Chromatography 1

By adding a buffer solution (200 mmol/L sodium phosphate buffer, pH 5.5) and another buffer solution (20 mmol/L sodium phosphate buffer, pH 6.0) to the antithrombin-containing aqueous solution 4 obtained in Example 1 (16.0 mg as the antithrombin composition), the pH was adjusted to 6.0, and the conductivity was adjusted to 6.1 mS/cm. The obtained solution was passed through a Cellufine Sulfate m column (manufactured by Chisso, column volume 4 mL) which had been previously equilibrated with a buffer solution (20 mmol/L sodium phosphate buffer, pH 6.0), to thereby adsorb antithrombin to the column. After washing the column with a buffer solution (20 mmol/L sodium phosphate buffer, pH 6.0, 0.5 column volume), the antithrombin composition was eluted under a linear salt concentration gradient (10 column volumes) using a buffer solution (20 mmol/L sodium phosphate buffer, pH 6.0) and another buffer solution (1 mol/L sodium chloride, 20 mmol/L sodium phosphate buffer, pH 6.0). The eluate was evenly fractionated in 2 ml at the start of elution. Amount of the antithrombin composition in each fraction was measured using a reverse HPLC method [J. Chromatography B, 662, 209 (1994)], the α-form content rate using a hydroxyapatite HPLC method [Protein Expression and Purification, 28, 196 (2003), JP-T-2003-520806], and the binding number of sialic acids was measured using a fluorescent HPLC method [Anal. Biochem., 164, 138 (1987)]. The results were shown in Table 1.

TABLE 1

Results of Cellufine Sulfate chromatography of Example 2

| | Conductivity (mS/cm) | Amount of Antithrombin Composition (mg) | α-form Content Rate (%) | β-form Content Rate (%) | Binding Number of Sialic Acids | Number of Sialic Acids per Sugar Chain |
|---|---|---|---|---|---|---|
| Antithrombin-Containing Aqueous Solution 4 | 6.1 | 16.0 | 70.9 | 29.1 | 5.53 | 1.49 |
| Elution Fraction (EF) 11 | 4.3 | 0.20 | 100 | 0 | 6.11 | 1.53 |
| EF 12 | 8.2 | 1.26 | 99.3 | 0.7 | 7.49 | 1.88 |
| EF 13 | 12.1 | 1.82 | 94.9 | 5.1 | 7.34 | 1.86 |
| EF 14 | 16.0 | 2.18 | 94.5 | 5.5 | 6.76 | 1.71 |
| EF 15 | 19.9 | 2.08 | 98.6 | 1.4 | 6.12 | 1.54 |
| EF 16 | 23.8 | 1.74 | 100 | 0 | 5.38 | 1.35 |
| EF 17 | 27.8 | 1.36 | 75.7 | 24.3 | 4.82 | 1.28 |
| EF 18 | 31.7 | 1.44 | 28.4 | 71.6 | 5.35 | 1.63 |
| EF 19 | 35.6 | 1.52 | 0 | 100 | 5.15 | 1.72 |
| EF 20 | 39.5 | 0.92 | 0 | 100 | 4.45 | 1.48 |
| EF 21 | 43.4 | 0.48 | 0 | 100 | 4.10 | 1.37 |

The α-form content rate, α-form recovery rate and the binding number of sialic acids of the antithrombin composition obtained by mixing respective elution fractions shown in Table 1, were shown in Table 2. As shown in Table 2, for example by mixing fractions 11 to 17, an antithrombin composition having an α-form content rate of 94.5% and the binding number of sialic acids of 6.33 (the number of sialic acids per sugar chain of 1.61) was obtained with an α-form recovery rate of 88.7%. Based on the above, an antithrombin composition having desired α-form content rate and the binding number of sialic acids can be obtained with a high yield by mixing appropriate elution fractions.

TABLE 2

Antithrombin composition prepared by Cellufine Sulfate chromatography of Example 2 (1)

| | α-Form Content Rate (%) | α-Form Recovery Rate (%) | Binding Number of Sialic Acids | Number of Sialic Acids per Sugar Chain |
|---|---|---|---|---|
| Antithrombin-Containing Aqueous Solution 4 | 70.9 | — | 5.53 | 1.49 |
| Elution Fraction (EF) 11-17 | 94.5 | 88.7 | 6.33 | 1.61 |
| EF 11-18 | 86.7 | 92.3 | 6.22 | 1.61 |

Next, β-form content rate, β-form recovery rate and the binding number of sialic acids of the antithrombin composition obtained by mixing the elution fractions shown in Table 1, were shown in Table 3. As shown in Table 3, for example by mixing fractions 18 to 21, an antithrombin composition having a β-form content rate of 90.6% and the binding number of sialic acids of 4.95 (the number of sialic acids per sugar chain of 1.60) was obtained with a β-form recovery rate of 84.9%. Based on the above, an antithrombin composition having desired β-form content rate and the binding number of sialic acids can be obtained with a high yield by mixing appropriate elution fractions.

TABLE 3

Antithrombin composition prepared by Cellufine Sulfate chromatography of Example 2 (2)

| | β-Form Content Rate (%) | β-Form Recovery Rate (%) | Binding Number of Sialic Acids | Number of Sialic Acids per Sugar Chain |
|---|---|---|---|---|
| Antithrombin-Containing Aqueous Solution 4 | 29.1 | — | 5.53 | 1.49 |
| Elution Fraction (EF) 17-21 | 74.9 | 92.0 | 4.92 | 1.51 |
| EF 18-21 | 90.6 | 84.9 | 4.95 | 1.60 |

Example 3

Preparation of Antithrombin Composition by Cellufine Sulfate Chromatography 2

By adding a buffer solution (200 mmol/L sodium phosphate buffer, pH 5.5) and another buffer solution (1 mmol/L sodium chloride, 20 mmol/L sodium phosphate buffer, pH 6.0) to the antithrombin-containing aqueous solution 4 obtained in Example 1 [amount of antithrombin composition: 196 mg (Purification example 1 shown in Table 4) or 117 mg (Purification example 2 shown in Table 4)], the pH and conductivity were adjusted. After contacting the obtained solution with a Cellufine Sulfate m column (manufactured by Chisso, column volume 20 mL) which had been previously equilibrated with a buffer solution (20 mmol/L sodium phosphate buffer, pH 6.0, its conductivity was adjusted by adding sodium chloride), the unadsorbed fractions were collected to obtain the antithrombin composition. Amount of the antithrombin composition in the unadsorbed fractions was measured using a reverse HPLC method [J. Chromatography B, 662, 209 (1994)], the α-form content rate using a hydroxyapatite HPLC method [Protein Expression and Purification, 28, 196 (2003), JP-T-2003-520806], and the binding number of sialic acids was measured using a fluorescent HPLC method [Anal. Biochem., 164, 138 (1987)].

The conductivity of the antithrombin-containing aqueous solution and loaded amount of the antithrombin composition per 1 ml carrier, α-form content rate of the unadsorbed fraction, the binding number of sialic acids and α-form recovery rate were shown in Table 4. As shown in Table 4, the antithrombin composition having an α-form content rate of 90% or more and 1.5 or more as the number of sialic acid molecules per sugar chain in the unadsorbed fraction was obtained with a high recovery rate, by adjusting conductivity of the antithrombin-containing aqueous solution and the loaded amount per unit volume of the carrier.

TABLE 4

Antithrombin composition prepared by Cellufine Sulfate chromatography described in Example 3

| Purification Example | 1 | 2 |
|---|---|---|
| Conductivity of Antithrombin-Containing Aqueous Solution 4 (mS/cm) | 19.1 | 19.1 |
| Loaded Amount per 1 ml Cellufine Sulfate Carrier (mg/mL) | 9.8 | 5.9 |
| α-Form Content Rate (%) before Purification | 68.9 | 70.4 |
| Binding Number of Sialic Acids before Purification | 4.64 | 5.48 |
| Number of Sialic Acids per Sugar Chain before Purification | 1.26 | 1.48 |
| α-Form Content Rate (%) in Unadsorbed Fraction | 91.2 | 95.3 |
| Binding Number of Sialic Acids in Unadsorbed Fraction | 5.85 | 6.56 |
| Number of Sialic Acids per Sugar Chain in Unadsorbed Fraction | 1.50 | 1.66 |
| α-Form Recovery Rate (%) of Unadsorbed Fraction | 95.6 | 67.8 |

Comparative Example 1

Preparation of Antithrombin Composition by Heparin Chromatography (1)

The antithrombin-containing aqueous solution 1 obtained in Example 1 (amount of the antithrombin composition: 17.7 mg) was passed through a heparin column (Heparin Sepharose 6 Fast Flow, manufactured by GE Healthcare, column volume 4 ml) which had been previously equilibrated with a buffer solution (50 mmol/L Tris, 14 mmol/L sodium citrate buffer, pH 7.4), to thereby adsorb the antithrombin composition onto the column. After washing with a buffer solution (50 mmol/L Tris, 14 mmol/L sodium citrate buffer, pH 7.4, 10 column volumes), the antithrombin composition was eluted under a linear salt concentration gradient (10 column volume) using a buffer solution (50 mmol/L Tris, 14 mmol/L sodium citrate buffer, pH 7.4) and another buffer solution (2.5 mol/L sodium chloride, 50 mmol/L Tris, 14 mmol/L sodium citrate buffer, pH 7.4). The eluate was evenly fractionated in 2 ml at the start of elution. Amount of the antithrombin composition in each fraction was measured using a reverse HPLC method [J. Chromatography B, 662, 209 (1994)], the α-form content rate using a hydroxyapatite HPLC method [Protein Expression and Purification, 28, 196 (2003), JP-T-2003-520806], and the binding number of sialic acids was measured using a fluorescent HPLC method [Anal. Biochem., 164, 138 (1987)]. The results thereof were shown in Table 5.

TABLE 5

Results of the heparin chromatography of Comparative Example 1

| | Conductivity (mS/cm) | Amount of Antithrombin Composition (mg) | α-Form Content Rate (%) | β-Form Content Rate (%) | Binding Number of Sialic Acids | Number of Sialic Acids per Sugar Chain |
|---|---|---|---|---|---|---|
| Antithrombin-Containing Aqueous Solution 1 | — | 17.7 | 71.0 | 29.0 | 5.50 | 1.48 |

TABLE 5-continued

Results of the heparin chromatography of Comparative Example 1

| | Conductivity (mS/cm) | Amount of Antithrombin Composition (mg) | α-Form Content Rate (%) | β-Form Content Rate (%) | Binding Number of Sialic Acids | Number of Sialic Acids per Sugar Chain |
|---|---|---|---|---|---|---|
| Elution Fraction (EF) 10 | 63.7 | 1.71 | 91.2 | 8.8 | 7.62 | 1.95 |
| EF 11 | 75.3 | 1.79 | 95.5 | 4.5 | 7.52 | 1.90 |
| EF 12 | 86.8 | 1.46 | 92.0 | 8.0 | 7.12 | 1.82 |
| EF 13 | 98.4 | 1.13 | 74.6 | 5.4 | 6.25 | 1.67 |
| EF 14 | 110.0 | 0.902 | 40.9 | 59.1 | 5.86 | 1.72 |
| EF 15 | 121.5 | 0.784 | 23.2 | 76.8 | 5.57 | 1.72 |
| EF 16 | 133.1 | 0.636 | 14.5 | 85.5 | 5.18 | 1.65 |
| EF 17 | 144.7 | 0.459 | 12.3 | 87.7 | 5.27 | 1.69 |
| EF 18 | 156.3 | 0.316 | 12.6 | 87.4 | 4.85 | 1.55 |

α-Form content rate, α-form recovery rate and the binding number of sialic acids of the antithrombin composition obtained by mixing the elution fractions mainly containing the α-form were shown in Table 6. As shown in Table 6, by mixing elution fractions 10 to 12, an antithrombin composition having the α-form content rate of 93.0% and the binding number of sialic acids of 7.44 (the number of sialic acids per sugar chain, 1.89) could be obtained, but the α-form recovery rate was 36.4%.

TABLE 6

Antithrombin composition prepared by heparin chromatography of Comparative Example 1 (1)

| | α-form Content Rate (%) | α-form Recovery Rate (%) | Binding Number of Sialic Acids | Number of Sialic Acids per Sugar Chain |
|---|---|---|---|---|
| Antithrombin-Containing Aqueous Solution 1 | 71.6 | — | 5.50 | 1.48 |
| Elution Fraction (EF) 10-12 | 93.0 | 36.4 | 7.44 | 1.89 |
| EF 10-13 | 89.6 | 43.0 | 7.22 | 1.85 |
| EF 10-14 | 83.3 | 45.9 | 7.04 | 1.84 |

In addition, β-form content rate, β-form recovery rate and the binding number of sialic acids of the antithrombin composition obtained by mixing the elution fractions mainly containing the β-form were shown in Table 7. As shown in Table 7, by mixing elution fractions 16 to 18, the antithrombin composition having a β-form content rate of 86.7% and the binding number of sialic acids (the number of sialic acids per sugar chain of 1.64) of 5.14 could be obtained, but the β-form recovery rate was 24.3%.

TABLE 7

Antithrombin composition prepared by heparin chromatography of Comparative Example 1 (2)

| | β-form Content Rate (%) | β-form Recovery Rate (%) | Binding Number of Sialic Acids | Number of Sialic Acids per Sugar Chain |
|---|---|---|---|---|
| Antithrombin-Containing Aqueous Solution 1 | 28.4 | — | 5.50 | 1.48 |
| Elution Fraction (EF) 14-18 | 76.1 | 46.8 | 5.46 | 1.68 |
| EF 15-18 | 83.1 | 36.2 | 5.29 | 1.67 |
| EF 16-18 | 86.7 | 24.3 | 5.14 | 1.64 |

Example 4

Preparation of High Purity Antithrombin Composition by a Combination of Cellufine Sulfate Chromatography and Hydrophobic Chromatography (1)

An antithrombin composition was prepared from the antithrombin-containing aqueous solution 4 obtained in Example 1 (amount of the antithrombin composition: 16 mg) in the same manner as the method described in Example 2. The elution fractions 11 to 17 obtained by a Cellufine Sulfate chromatography were mixed, and a buffer solution (3 mol/L ammonium sulfate, 20 mmol/L sodium phosphate buffer, pH 6.7) was added thereto to adjust an ammonium sulfate final concentration of 2 mol/L. The obtained solution was passed through a hydrophobic column [Phenyl Sepharose (low-sub), manufactured by GE Healthcare, column volume 4 ml] which had been previously equilibrated with a buffer solution (2 mol/L ammonium sulfate, 20 mmol/L sodium phosphate buffer, pH 6.8), to thereby adsorb antithrombin onto the column. After washing with a buffer solution (2 mol/L ammonium sulfate, 20 mmol/L sodium phosphate buffer, pH 6.8, 3 column volumes), an antithrombin composition was obtained by eluting under a linear salt concentration gradient (10 column volumes) using a buffer solution (2 mol/L ammonium sulfate, 20 mmol/L sodium phosphate buffer, pH 6.8) and another buffer solution (20 mmol/L sodium phosphate buffer, pH 6.8). The latent form content rate contained in the composition was measured by a hydrophobic HPLC method [Protein Expression and Purification, 21, 149 (2001), and the associated form content rate by a gel filtration HPLC method. In addition, the α-form content rate was measured using a hydroxyapatite HPLC method [Protein Expression and Purification, 28, 196 (2003), JP-T-2003-520806], and the binding number of sialic acids was measured using a fluorescent HPLC method [Anal. Biochem., 164, 138 (1987)]. The results were shown in Table 8. As shown in Table 8, an antithrombin composition having improved purity, while keeping its α-form content rate and the binding number of sialic acids, was prepared by further carrying out hydrophobic chromatography of the antithrombin composition obtained from the adsorbed fractions of the Cellufine Sulfate chromatography.

TABLE 8

Results of the hydrophobic chromatography of Example 4

| | α-Form Content Rate (%) | Binding Number of Sialic Acids | Number of Sialic Acids per Sugar Chain | Latent Form Content Rate | Associated Form Content Rate |
|---|---|---|---|---|---|
| Before Purification | 100 | 6.45 | 1.61 | 26.3 | 4.2 |
| After Purification | 100 | 7.58 | 1.90 | 0 | N.D. |

Example 5

Preparation of High Purity Antithrombin Composition by a Combination of Cellufine Sulfate Chromatography and Hydrophobic Chromatography (2)

An antithrombin composition was prepared from unadsorbed fractions of the antithrombin-containing aqueous solution 4 obtained in Example 1 (amount of the antithrombin composition: 180 mg) in the same manner as the method shown in Example 3 (column volume: 20 mL, loaded amount of antithrombin per 1 ml carrier: 9 mg, conductivity of the antithrombin composition: 19.7 mS/cm). A buffer solution (3 mol/L ammonium sulfate, 20 mmol/L sodium phosphate buffer, pH 6.7) was added to the fractions to prepare an ammonium sulfate solution of a final concentration of 2 mol/L. The obtained solution was passed through a hydrophobic column [Phenyl Sepharose (low-sub), manufactured by GE Healthcare, column volume 4 ml] which had been previously equilibrated with a buffer solution (2 mol/L ammonium sulfate, 20 mmol/L sodium phosphate buffer, pH 6.8), to thereby adsorb the antithrombin composition onto the column. After washing with a buffer solution (2 mol/L ammonium sulfate, 20 mmol/L sodium phosphate buffer, pH 6.8, 3 column volumes), an antithrombin composition was obtained by eluting under a linear salt concentration gradient (10 column volumes) using a buffer solution (2 mol/L ammonium sulfate, 20 mmol/L sodium phosphate buffer, pH 6.8) and another buffer solution (20 mmol/L sodium phosphate buffer, pH 6.8). The latent form content rate contained in the composition was measured by a hydrophobic HPLC method [Protein Expression and Purification, 21, 149 (2001), and the associated form content rate by a gel filtration HPLC method. In addition, the α-form content rate was measured using a hydroxyapatite HPLC method [Protein Expression and Purification, 28, 196 (2003), JP-T-2003-520806], and the binding number of sialic acids using a fluorescent HPLC method [Anal. Biochem., 164, 138 (1987)]. The results were shown in Table 9. As shown in Table 9, an antithrombin composition having improved purity, while keeping its α-form content rate and the binding number of sialic acids, was prepared by further carrying out a hydrophobic chromatography of the antithrombin composition obtained from the unadsorbed fractions of the Cellufine Sulfate chromatography.

TABLE 9

Results of the hydrophobic chromatography of Example 5

| | α-Form Content Rate (%) | Binding Number of Sialic Acids | Number of Sialic Acids per Sugar Chain | Latent Form Content Rate | Associated Form Content Rate |
|---|---|---|---|---|---|
| Before Purification | 96.7 | 6.23 | 1.57 | 14.6 | 10.1 |
| After Purification | 97.9 | 6.21 | 1.56 | 0.2 | N.D. |

Example 6

Preparation of High Purity Antithrombin Composition by a Combination of Cellufine Sulfate Chromatography and Hydrophobic Chromatography (3)

The antithrombin-containing aqueous solution 5 obtained in Example 1 (amount of the antithrombin composition: 76.0 mg) was adjusted to the pH of 6.0 and to the conductivity of 7 mS/cm or lower, by adding a buffer solution (200 mmol/L sodium phosphate buffer, pH 5.5) and another buffer solution (20 mmol/L sodium phosphate buffer, pH 6.0). This solution was passed through a Cellufine Sulfate m column [manufactured by Chisso, column volume 19 ml] which had been previously equilibrated with a buffer solution (20 mmol/L sodium phosphate buffer, pH 6.0), to thereby adsorb antithrombins onto the column. After washing the column with a buffer solution (20 mmol/L sodium phosphate buffer, pH 6.0), an antithrombin composition was eluted under a linear salt concentration gradient using a buffer solution (20 mmol/L sodium phosphate buffer, pH 6.0) and another buffer solution (1 mol/L sodium chloride, 20 mmol/L sodium phosphate buffer, pH 6.0). The eluate was evenly fractionated in 0.5 column volume (9.5 ml). A buffer solution (100 g/l glycine buffer solution, pH 9.0) was added at a ratio of 1 mL to 5 mL of the fractionated solution. Amount of the antithrombin composition in each fraction solution was measured by a reverse phase HPLC method [J. Chromatography B, 662, 209 (1994), and the α-form and β-form content rates were measured using a hydroxyapatite HPLC method [Protein Expression and Purification, 28, 196 (2003), JP-T-2003-520806]. Fractions having an α-form content rate of 90% or more were combined and used as an antithrombin composition A. Also, fractions having a β-form content rate of 85% or more were combined and used as an antithrombin composition B.

By adding a buffer solution (1.5 mol/L sodium citrate, 20 mmol/L sodium phosphate buffer, pH 7.0) to the thus obtained antithrombin composition A (amount of antithrombin: 8.0 mg), a composition containing 1 mol/L in final concentration of sodium citrate was prepared. This solution was passed through a hydrophobic column [Phenyl Sepharose 6 Fast Flow (low-sub), manufactured by GE Healthcare, column volume 4 mL] which had been previously equilibrated with a buffer solution (2 mol/L ammonium sulfate, 50 mmol/L sodium phosphate buffer, pH 7.0), to thereby adsorb the antithrombin composition to the column. After washing the column with a buffer solution (2 mol/L ammonium sulfate, 50 mmol/L sodium phosphate buffer, pH 7.0), an antithrombin composition C was obtained by eluting under a linear salt concentration gradient using a buffer solution (2 mol/L ammonium sulfate, 50 mmol/L sodium phosphate buffer, pH 7.0) and another buffer solution (20 mmol/L sodium phosphate buffer, pH 7.0). Amount of the antithrombin composition contained in the composition was measured using a reverse phase HPLC method [J. Chromatography B, 662, 209 (1994), and the latent form content rate using a hydrophobic HPLC method [Protein Expression and Purification, 21, 149 (2001)], and the associated form content rate using a gel filtration HPLC method. In addition, the α-form content rate was measured using a hydroxyapatite HPLC method [Protein Expression and Purification, 28, 196 (2003), JP-T-2003-520806], and the binding number of sialic acids using a fluorescent HPLC method [Anal. Biochem., 164, 138 (1987)].

Comparative Example 2

Preparation of Antithrombin Composition by Heparin Chromatography (2)

The antithrombin-containing aqueous solution 5 obtained in Example 1 (amount of the antithrombin composition: 74.0 mg) was adjusted to pH 6.0 and to a conductivity of 7 mS/cm or less, by adding a buffer solution (200 mmol/L sodium phosphate buffer, pH 5.5) and another buffer solution (20 mmol/L sodium phosphate buffer, pH 6.0). This solution was passed through a heparin column [Heparin Sepharose 6 Fast Flow, manufactured by GE Healthcare, column volume 18.5 ml] which had been previously equilibrated with a buffer solution (20 mmol/L sodium phosphate buffer, pH 6.0), to thereby adsorb antithrombin to the column. After washing the column with a buffer solution (20 mmol/L sodium phosphate buffer, pH 6.0), an antithrombin composition was obtained by eluting the antithrombin composition under a linear salt concentration gradient using a buffer solution (20 mmol/L sodium phosphate buffer, pH 6.0) and another buffer solution (2.5 mol/L sodium chloride, 20 mmol/L sodium phosphate buffer, pH 6.0). The eluate was evenly fractionated in 0.5 column volume (9.25 ml). A buffer solution (100 g/L glycine buffer solution, pH 9.0) was added at a ratio of 1 mL to 5 mL of the fractionated solution. Amount of the antithrombin composition in each fraction solution was measured by a reverse phase HPLC method [J. Chromatography B, 662, 209 (1994), and the α-form and β-form content rates were measured using a hydroxyapatite HPLC method [Protein Expression and Purification, 28, 196 (2003), JP-T-2003-520806]. Fractions having an α-form content rate of 90% or more were combined and used as an antithrombin composition D. Also, fractions having a β-form content rate of 85% or more were combined and used as an antithrombin composition E.

By adding a buffer solution (1.5 mol/L sodium citrate, 20 mmol/L sodium phosphate buffer, pH 7.0) to the thus obtained antithrombin composition D (amount of the antithrombin composition: 8.0 mg), a composition containing 1 mol/L in final concentration of sodium citrate was prepared. This solution was passed through a hydrophobic column [Phenyl Sepharose 6 Fast Flow (low-sub), manufactured by GE Healthcare, column volume 4 mL] which had been previously equilibrated with a buffer solution (2 mol/L ammonium sulfate, 50 mmol/L sodium phosphate buffer, pH 7.0), to thereby adsorb the antithrombin composition to the column. After washing the column with a buffer solution (2 mol/L ammonium sulfate, 50 mmol/L sodium phosphate buffer, pH 7.0), an antithrombin composition F was obtained by eluting the antithrombin composition under a linear salt concentration gradient using a buffer solution (2 mol/L ammonium sulfate, 50 mmol/L sodium phosphate buffer, pH 7.0) and another buffer solution (20 mmol/L sodium phosphate buffer, pH 7.0) Amount of the antithrombin composition contained in the composition was measured using a reverse phase HPLC method [J. Chromatography B, 662, 209 (1994), the latent form content rate using a hydrophobic HPLC method [Protein Expression and Purification, 21, 149 (2001)], and the associated form content rate using a gel filtration HPLC method. In addition, the α-form content rate was measured using a hydroxyapatite HPLC method [Protein Expression and Purification, 28, 196 (2003), JP-T-2003-520806], and the binding number of sialic acids using a fluorescent HPLC method [Anal. Biochem., 164, 138 (1987)].

Results of the antithrombin composition A having an α-form content rate of 90% or more, prepared from the antithrombin-containing aqueous solution 5 using Cellufine Sulfate chromatography, and the antithrombin composition D having an α-form content rate of 90% or more, prepared from the antithrombin-containing aqueous solution 5 using heparin chromatography, were shown in Table 10. As shown in Table 10, the recovery rate of the case of using Cellufine Sulfate chromatography was 19.1% higher than the case of the use of heparin chromatography shown by Comparative Example 2. The α-form content rate and the binding number of sialic acids were almost the same. In addition, in the case of the use of Cellufine Sulfate chromatography, the volume of the combined elution fractions was reduced by ⅔.

TABLE 10

Results of Cellufine Sulfate chromatography/heparin chromatography of Example 6 and Comparative Example 2 (1)

|  | Chromatography | Recovery rate (%) | Volume | α-Form Content Rate (%) | Binding Number of Sialic Acids |
|---|---|---|---|---|---|
| Antithrombin Composition A | Cellufine Sulfate | 59.8 | 3.0 Column Volume | 94 | 5.84 |
| Antithrombin Composition D | Heparin | 40.7 | 4.5 Column Volume | 96 | 6.03 |

Results of the antithrombin composition B having a β-form content rate of 85% or more, prepared from the antithrombin-containing aqueous solution 5 using Cellufine Sulfate chromatography, and the antithrombin composition E having a β-form content rate of 85% or more, prepared from the antithrombin-containing aqueous solution 5 using heparin chromatography, were shown in Table 11. As shown in Table 11, the recovery rate of the case of using Cellufine Sulfate chromatography was 7.0% higher than the case of using heparin chromatography shown by Comparative Example 2. The β-form content rate and the binding number of sialic acids were almost the same. The results were shown in Table 11.

TABLE 11

Results of Cellufine Sulfate chromatography/heparin chromatography of Example 6 and Comparative Example 2 (2)

|  | Chromatography | Recovery rate (%) | Volume | β-form Content Rate (%) | Binding Number of Sialic Acids |
|---|---|---|---|---|---|
| Antithrombin Composition B | Cellufine Sulfate | 22.2 | 2.5 Column Volume | 75 | 4.27 |
| Antithrombin Composition E | Heparin | 15.2 | 3.0 Column Volume | 71 | 4.50 |

In addition, results of the antithrombin composition C prepared from the antithrombin-containing aqueous solution 5 using Cellufine Sulfate chromatography and hydrophobic chromatography, and results of the antithrombin composition F prepared from the antithrombin-containing aqueous solution 5 using heparin chromatography and hydrophobic chromatography, were shown in Table 12. As shown in Table 12, at the recovery rate of the antithrombin α-form, the case of using Cellufine Sulfate chromatography and hydrophobic chromatography was 12.1% higher than the case of using heparin chromatography and hydrophobic chromatography as shown by Comparative Example 2. The α-form content rate, the binding number of sialic acids, the latent form content rate and the associated form content rate were almost the same.

TABLE 12

Results of hydrophobic chromatography of Example 6 and Comparative Example 2

| | Chromatography | Recovery Rate (%) | α-Form Content Rate (%) | Binding Number of Sialic Acids | Latent Form Content Rate | Associated Form Content Rate |
|---|---|---|---|---|---|---|
| Antithrombin Composition C | Cellufine Sulfate - Hydrophobic | 38.5 | 100 | 6.00 | 0.2 | N.D. |
| Antithrombin Composition F | Heparin - Hydrophobic | 26.4 | 100 | 6.08 | 0.2 | N.D. |

Example 7

Preparation of High Purity Antithrombin Composition by a Combination of Cellufine Sulfate Chromatography and Hydrophobic Chromatography (4)

By adding a buffer solution (1.5 mol/L sodium citrate, 20 mmol/L sodium phosphate buffer, pH 7.0) to the antithrombin-containing aqueous solution 5 obtained in Example 1 (amount of antithrombin composition: 226 mg), a composition containing 1 mol/L in final concentration of sodium citrate was prepared. The obtained solution was passed through a hydrophobic column [Phenyl Sepharose 6 Fast Flow (low-sub), manufactured by GE Healthcare, column volume 23.7 mL] which had been previously equilibrated with a buffer solution (2 mol/L ammonium sulfate, 50 mmol/L sodium phosphate buffer, pH 7.0), to thereby adsorb the antithrombin composition onto the column. After washing the column with a buffer solution (2 mol/L ammonium sulfate, 50 mmol/L sodium phosphate buffer, pH 7.0), an antithrombin composition was obtained by eluting the antithrombin composition under a linear salt concentration gradient using a buffer solution (2 mol/L ammonium sulfate, 50 mmol/L sodium phosphate buffer, pH 7.0) and another buffer solution (20 mmol/L sodium phosphate buffer, pH 7.0). Concentration of the antithrombin composition contained in the above composition was measured using a UV method.

The obtained antithrombin composition (amount of the antithrombin composition: 76 mg) was concentrated 10-fold using an ultrafiltration membrane (Biomax 10, manufactured by Millipore), and then 10 volumes of a buffer solution (20 mmol/L sodium phosphate buffer, pH 6.0) was added thereto. By repeating this step 3 times, desalting was carried out (exchange rate: 1000 times). The obtained desalted solution was passed through a Cellufine Sulfate m column (manufactured by Chisso, column volume 19 ml) which had been previously equilibrated with a buffer solution (20 mmol/L sodium phosphate buffer, pH 6.0), to thereby adsorb antithrombin onto the column. After washing the column with a buffer solution (20 mmol/L sodium phosphate buffer, pH 6.0), an antithrombin composition was eluted under a linear salt concentration gradient using a buffer solution (20 mmol/L sodium phosphate buffer, pH 6.0) and another buffer solution (1 mol/L sodium chloride, 20 mmol/L sodium phosphate buffer, pH 6.0). The eluate was evenly fractionated in 0.5 column volume (9.5 ml). To 5 ml of the fractionated solution, 1 ml of a buffer solution (100 g/l glycine buffer solution, pH 9.0) was added. Amount of the antithrombin composition in each fractionated solution was measured using a reverse HPLC method [J. Chromatography B, 662, 209 (1994)], and the α-form and β-form content rates was measured using a hydroxyapatite HPLC method [Protein Expression and Purification, 28, 196 (2003), JP-T-2003-520806]. Fractions having an α-form content of 90% or more were combined and used as an antithrombin composition G.

Results of the antithrombin composition C prepared from the antithrombin-containing aqueous solution 5 in Example 6 by carrying out the Cellufine Sulfate chromatography and hydrophobic chromatography in this order and results of the antithrombin composition G prepared from the antithrombin-containing aqueous solution 5 by carrying out the hydrophobic chromatography and the Cellufine Sulfate chromatography in this order were shown in Table 13. As shown in Table 13, the recovery rate, α-form content, binding number of sialic acids and latent form content of the antithrombin composition G prepared by carrying out the hydrophobic chromatography and the Cellufine Sulfate chromatography in this order were similar to those of the antithrombin composition C prepared by carrying out the Cellufine Sulfate chromatography and the hydrophobic chromatography in this order as shown in Example 6. The associated form content was lower in the antithrombin composition C.

TABLE 13

Results of the Cellufine Sulfate chromatography and hydrophobic chromatography of Example 7

| | Chromatography | Recovery Rate (%) | α-form Content Rate (%) | Binding Number of Sialic Acids | Latent Form Content Rate | Associated Form Content Rate |
|---|---|---|---|---|---|---|
| Antithrombin Composition C | Cellufine Sulfate - Hydrophobic | 38.5 | 100 | 6.00 | 0.2 | N.D. |
| Antithrombin Composition G | Hydrophobic - Desalt - Cellufine Sulfate | 36.8 | 100 | 6.21 | 0.9 | 2.9 |

While the invention has been described in detail and with reference to specific embodiments thereof, it will be apparent to one skill in the art that various changes and modifications can be made therein without departing from the spirit and scope thereof.

This application is based on Japanese patent application No. 2007-096179 filed Apr. 2, 2007, the entire contents of which is incorporated hereinto by reference. All references cited herein are incorporated in their entirety.

INDUSTRIAL APPLICABILITY

The invention provides an antithrombin composition having a desired α-form content rate or β-form content rate which can be obtained from antithrombin-containing aqueous solution.

The invention claimed is:

1. A process for producing an antithrombin composition, comprising
    contacting an antithrombin-containing aqueous solution with a cellulose sulfate ester chromatography carrier to obtain an antithrombin composition comprising antithrombin with an α-form content rate of at least 80%; and
    eluting the antithrombin compositions from a fraction adsorbed onto the carrier with an eluent having a conductivity of 0.01 mS/cm to 50 mS/cm to obtain an eluate with the antithrombin composition.

2. The process according to claim 1, which further comprises carrying out anion exchange chromatography and/or hydrophobic chromatography.

3. The process according to claim 2, wherein the hydrophobic chromatography is carried out after the cellulose sulfate ester chromatography.

4. The process according to claim 1,
    (a) wherein the antithrombin composition comprises an antithrombin in which sugar chains bound to the antithrombin contained in the composition have 1 or more to 3 or less sialic acids in average per sugar chain; or
    (b) wherein the antithrombin composition comprises an antithrombin in which sugar chains bound to the antithrombin contained in the composition have 1.5 or more to 2.5 or less sialic acids in average per sugar chain.

5. The process according to claim 4, wherein the sugar chains bound to the antithrombins are 3 or 4 sugar chains.

6. The process according to claim 1, wherein the antithrombin in the antithrombin composition has 3 or more to 12 or less sialic acids in average per antithrombin molecule.

7. The process according to claim 1, wherein the antithrombin in the antithrombin composition has 6 or more to 8 or less sialic acids in average per antithrombin molecule.

8. A process for producing an antithrombin composition, comprising contacting a conductivity-adjusted antithrombin-containing aqueous solution with a cellulose sulfate ester chromatography carrier to obtain an antithrombin composition comprising antithrombin with an α-form content rate of at least 80% from a fraction unadsorbed onto the carrier, and
    collecting the antithrombin composition from the fraction unadsorbed onto the carrier,
    wherein the conductivity-adjusted antithrombin-containing aqueous solution has a conductivity of 0.1 mS/cm to 50 mS/cm.

9. The process according to claim 8, which further comprises carrying out anion exchange chromatography and/or hydrophobic chromatography.

10. The process according to claim 9, wherein the hydrophobic chromatography is carried out after the cellulose sulfate ester chromatography.

11. The process according to claim 8,
    (a) wherein the antithrombin composition comprises an antithrombin in which sugar chains bound to the antithrombin contained in the composition have 1 or more to 3 or less sialic acids in average per sugar chain; or
    (b) wherein the antithrombin composition comprises an antithrombin in which sugar chains bound to the antithrombin contained in the composition have 1.5 or more to 2.5 or less sialic acids in average per sugar chain.

12. The process according to claim 11, wherein the sugar chains bound to the antithrombins are 3 or 4 sugar chains 13. The process according to claim 8, wherein the antithrombin in the antithrombin composition has 3 or more to 12 or less sialic acids in average per antithrombin molecule.

14. The process according to claim 8, wherein the antithrombin in the antithrombin composition has 6 or more to 8 or less sialic acids in average per antithrombin molecule.

* * * * *